United States Patent [19]

Hatchman

[11] Patent Number: 4,621,378
[45] Date of Patent: Nov. 11, 1986

[54] EYESHIELD

[76] Inventor: Robert A. Hatchman, 1410 S. 8th St., Arcadia, Calif. 91006

[21] Appl. No.: 613,301

[22] Filed: May 23, 1984

[51] Int. Cl.$^4$ .............................................. A61F 9/02
[52] U.S. Cl. .............................................. 2/9; 2/431; 2/12
[58] Field of Search ................... 2/9, 10, 12, 8, 206, 2/DIG. 11, 171, 181, 434, 426, 427, 431

[56] References Cited

U.S. PATENT DOCUMENTS

| | | | |
|---|---|---|---|
| 3,120,002 | 2/1964 | Blumenthal | 2/9 |
| 3,214,767 | 11/1965 | Weber | 2/9 |
| 3,369,255 | 2/1968 | Bolle | 2/9 |
| 4,076,373 | 2/1978 | Moretti | 2/434 X |
| 4,363,140 | 12/1982 | Correale | 2/9 |
| 4,393,519 | 7/1983 | Nicastro | 2/12 |

Primary Examiner—Peter Nerbun
Attorney, Agent, or Firm—Christie, Parker & Hale

[57] ABSTRACT

An eyeshield is provided which includes at least one and preferably a population of several like transparent lenses, each tinted or otherwise suited for a certain use or uses. Each of the lenses has an upper margin contoured to extend about and follow the frontal portion of the head, the upper margin terminating at opposite ends located near the temples. Each or both of the ends of the upper margin are provided with a slot. The eyeshield also includes an expandable, launderable headband fashioned from cloth inner and outer panels stitched together along their upper and side borders to cooperatively define a pocket to receive the upper margin of the lens. Projecting through the pocket is a pair of tacks disposed to be received into the slot located at each end of the lens. To mount a selected lens to a headband, one end of the lens margin is positioned in the pocket such that the tack registers with the slot. By expanding or stretching the pocket, the remainder of the upper margin of the lens is positioned in the pocket whereupon the tack at the other end registers with the slot of the remaining margin end.

13 Claims, 8 Drawing Figures

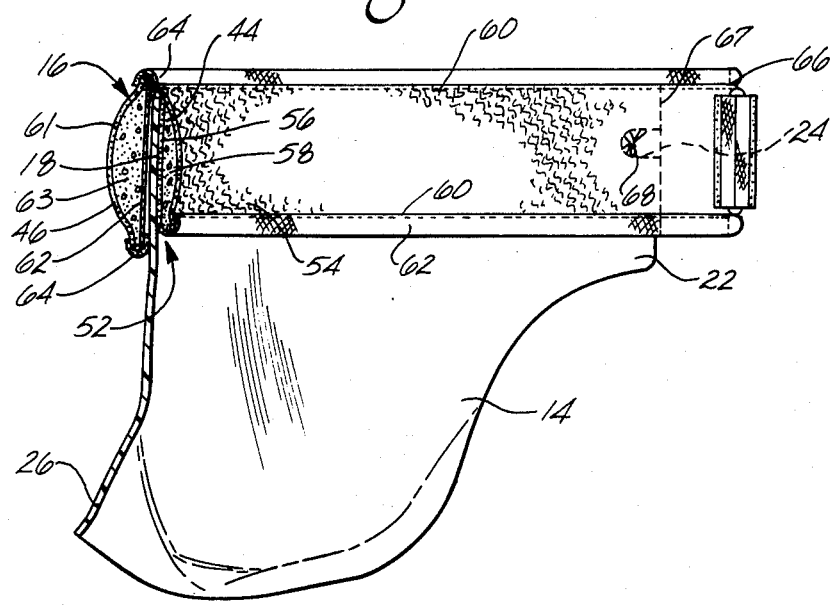
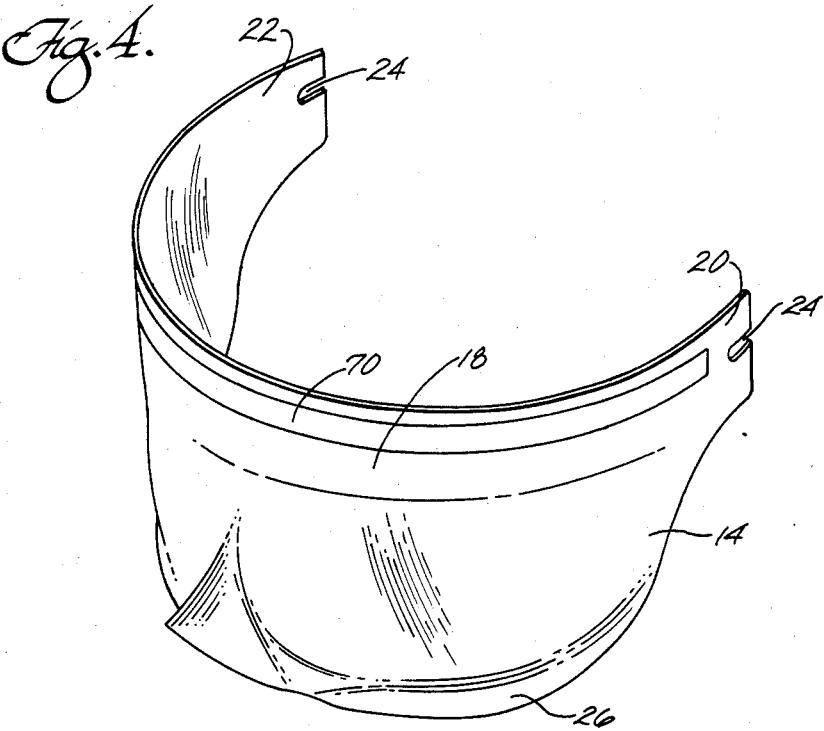

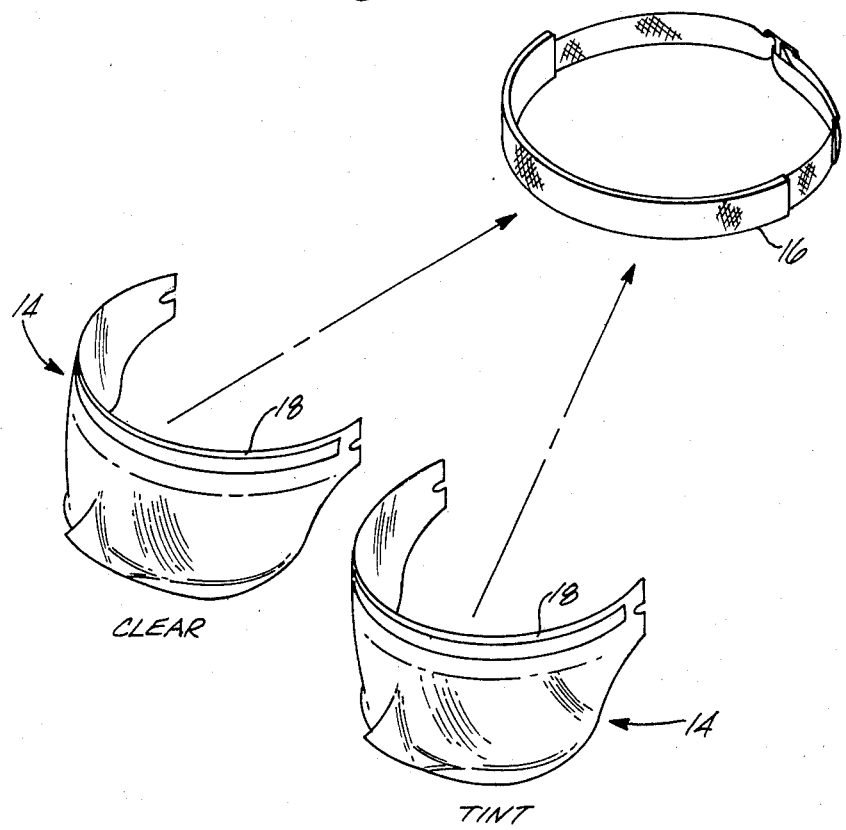

EYESHIELD

FIELD OF THE INVENTION

This invention relates to protective eyewear and more particularly to eyewear adapted to protect the eyes during athletic activity.

BACKGROUND OF THE INVENTION

In certain athletic activities it is desirable to shield or otherwise provide protection for the eyes. For example, during alpine or cross-country skiing, shielding the eyes from the wind or falling snow prevents the eyes from watering, enhances visibility and contributes overall to the enjoyment of the activity. In sports such as racquetball, squash, or tennis, it is desirable to protect the eyes from being struck by the ball or the opponent's racquet. Should either the ball or a racquet come in direct contact with the eye, severe damage may result.

Over and above athletic activities it is also desirable to provide eye protection in other settings such as in manufacturing plants, and household workshops.

One type of eyeshield provided in the prior art has an adjustable headband permanently mounting a transparent lens. The lens projects downwardly from the headband over the eyes and is adapted to bear upon the bridge of the nose. It has also been known to provide cooperative snaps between the headband and the lens to facilitate the interchange of lenses which are mounted to the headband. In addition to the permanent connection of the lens to the headband or the mechanical connection such as snaps or the like, it has been known to provide a headband having a cloth frontal portion incorporating a sweatband, the frontal portion of the headband being permanently glued over the upper margin of the lens. The headband also includes an adjustable strap to enlarge or contract the headband to fit different size heads.

The prior art eyeshields noted above have several drawbacks. Those providing for the permanent interconnection between the lens and the headband are not entirely satisfactory for all uses since, depending upon the conditions, tinted or clear lenses may be required. Also, from a fashion standpoint it may be desirable to change the color of the tint of the lenses. Those headbands having a permanent connection are not adapted to satisfy this desired end. Additionally, for those eyeshields with cloth headbands, it is often desirable to launder the headband. The permanent connection of the lens to the headband prohibits or at least frustrates such laundering.

Those eyeshields allowing for the removability or interchangeability or lenses encounter the drawback of being costly to manufacture. Additionally, they are typically cumbersome and unfashionable. For example, the lenses must be manufactured and provided with snaps positioned to mate with the cooperative snaps on the headband. This increases the overall manufacturing costs of the lens since all snaps of the lenses and headbands must be uniformly and precisely placed. Furthermore, the loss of one or more of the cooperative snaps from either the lens or the headband may render the eyeshield useless.

Another drawback of prior art eyeshields is that they are adapted to almost entirely bear against the bridge of the nose. Should an object strike the lens, the force resulting therefrom is substantially distributed to and concentrated at the bridge of the nose. As a result, a relatively small impact force may result in an injury to the nose.

SUMMARY OF THE INVENTION

There is, therefore, provided in the various embodiments of the present invention as hereinafter set forth, an eyeshield adapted to overcome the drawbacks noted above. The eyeshield includes at least one and preferably a population of several like transparent lenses, each tinted or otherwise suited for a certain use or uses. For example, one lens may be clear for use during night skiing, whereas another lense may be tinted for use during the day. Each of the lenses is adapted to cover and shield or otherwise protect the eyes from wind, flying objects, or the like. Each such lens has an upper margin contoured to extend about and follow the frontal portion of the head, the upper margin terminating at opposite ends located near the temples. Each or both of the ends of the upper margin are provided with a slot or tab generally oriented to extend from the rear toward the front of the head. Overall, the lens projects from the upper margin over the eyes to terminate at a lower border which flares outwardly from the face. The lens is shaped such that the border has a generally double "S" configuration to extend from the ends downwardly over the cheeks and nose bridge. When the lens is struck by an object, force is transmitted from the lens to the head by its upper margin and its lower border. In that the lower border is adapted to engage the face over the cheeks and nose bridge area, such a force is distributed to minimize damage to the face.

To mount a selected lens, the eyeshield includes an expandable headband adapted to encircle the head. The portion of the headband which encircles the frontal and temporal regions of the head defines a brow band. Preferably the brow band is fashioned from cloth inner and outer panels stitched together along their upper and side borders to cooperatively define a pocket to receive the upper margin of the lens. The inner panel is adapted to overlay the forehead and may be provided with perspiration absorbant material such as terrycloth and cushioning material to cushion the lens upper margin against the head. The outer panel may be similarly constructed. Positioned near each of the ends of the brow band and projecting through the pocket is a tack disposed to be received into the slot located at the ends of the lens. Alternatively, one of the ends of the brow band may be stitched or otherwise suitably constructed to define a receptacle adapted to closely receive a lens tab.

To mount a selected lens to a selected headband, one end of the lens margin is positioned in the pocket such that the tack registers with the slot or, alternatively, the tab is received into the recess. Expanding or stretching the brow band, which is advantageously provided for from its cloth construction, the remainder of the upper margin of the lens is positioned in the pocket whereupon the tack or pocket at the other end of the brow band registers with the slot or tab of the remaining margin end, securing the lens to the brow band. To enhance the connection of the lens to the brow band, the upper margin of the lens may be provided with a suitable, slightly adhesive surface. To remove the lens, the brow band is expanded to withdraw the tack at one end from the slot, freeing the lens from the brow band.

As can be appreciated, the cloth brow band is particularly well suited for removal from the lens for laundering thereof. Additionally, the foregoing construction promotes interchangeability of lenses and headbands as fashion or other conditions require. As still a further advantage, the eyeshield according to the present invention is inexpensive to manufacture.

BRIEF DESCRIPTION OF THE DRAWINGS

These and other features and advantages of the invention will become appreciated as the same becomes better understood by reference to the following detailed description, when read in conjunction with the drawings wherein:

FIG. 3 is a side section view of the eyeshield;

FIG. 4 is a perspective view of the lens for the eyeshield;

FIG. 8 illustrates the interchangeability of lenses with a headband.

DETAILED DESCRIPTION OF THE DRAWINGS

Figure 1:
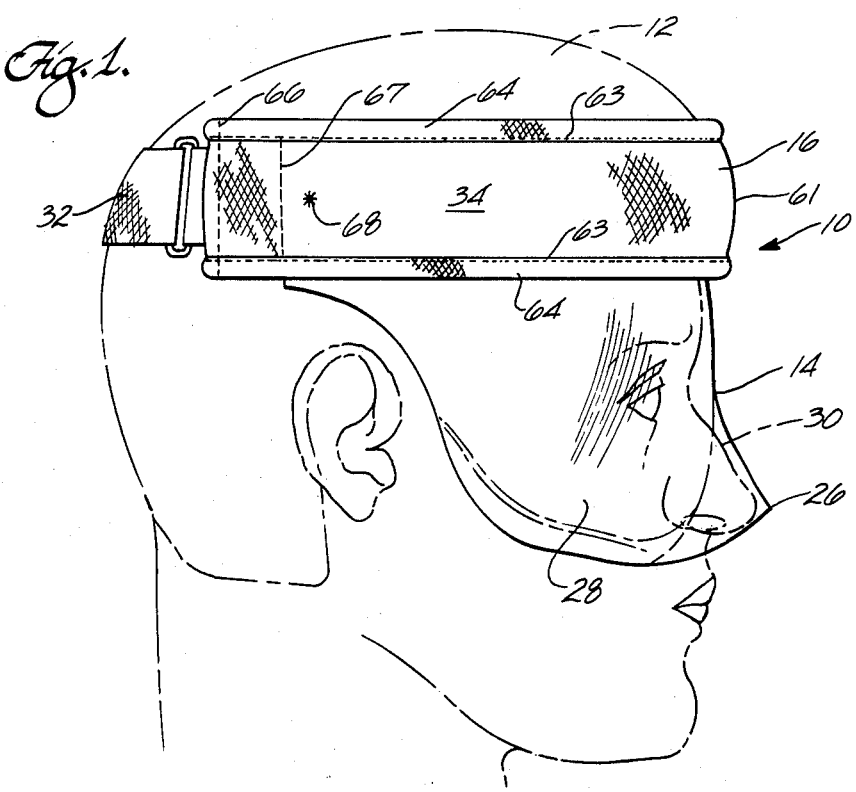
FIG. 1 is a side view of the eyeshield shown mounted to the head.
Figure 2:
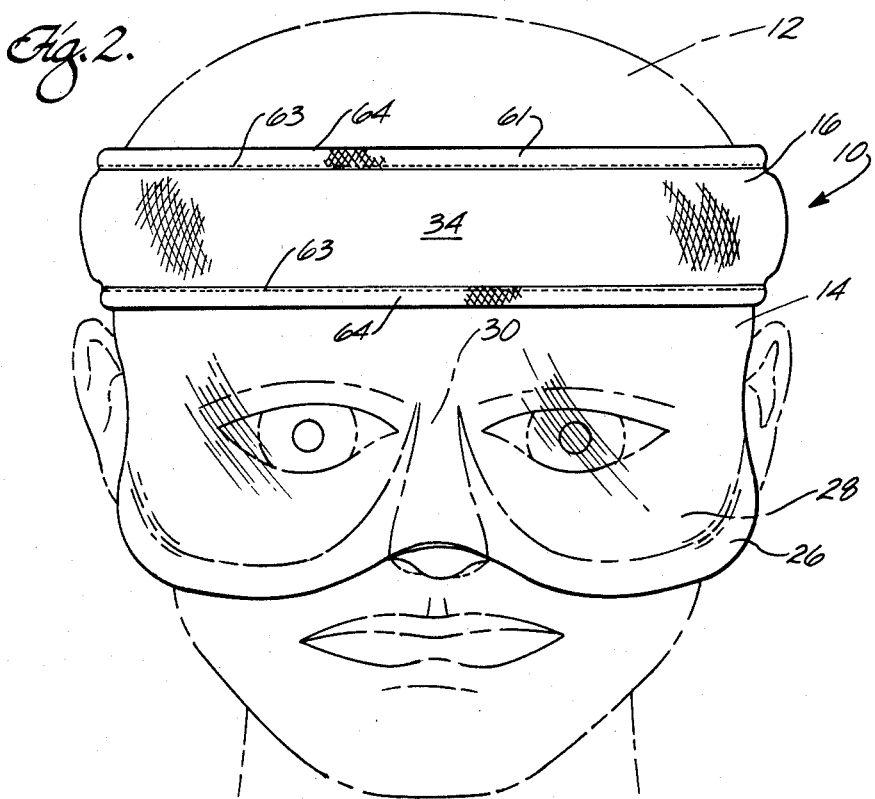
FIG. 2 is a front view of the eyeshield, also shown mounted to the head.

Turning to the drawings, FIGS. 1 and 2 illustrate an eyeshield 10 according to the present invention as mounted to an individual's head 12. The eyeshield 10 consists of a transparent lens 14 which is removably mounted to a headband 16. By securely mounting the eye shield 10 to the head 12 the lens 14 is positioned to protect and shield the eyes from sun, wind, flying objects, or the like. As a specific but not limiting example the eyeshield 10 is well suited for alpine skiing in that the lens 14 shields the eyes from wind that may be sufficiently cold to otherwise to cause the eyes to water. Furthermore, the lens may be tinted to shield the eyes from sunlight and glare. The removability of the lens 14 from the headband 16 promotes utility of the eyeshield 10 since the tint of the lens 14 may be altered based upon conditions such as sunlight or for fashion color coordination.

To provide the foregoing protection of the eyes, each such lens 14 as shown in FIGS. 1–4, is substantially arcuate to project over and around the eyes. The lens 14 has an upper margin 18 received by the headband 16 in a manner described in detail below to mount a selected lens 14 thereto. The upper margin 18 is adapted to be supported against the frontal portion of the head 12. The upper margin 18 terminates at right and left side tabs 20 and 22, each of which is positioned to lie approximately over a temporal area of the head 12. As shown in FIG. 4, the right and left side tabs 20 and 22 are substantially rectangular, parallel to each other and tangential to the overall curvature of the head 12. Disposed in the right side tab 20 is a slot 24 which projects forwardly into such tab. A similar slot 24 is likewise disposed in the same position and orientation in the left side tab 22.

From the cylindrical upper margin 18, the transparent lens 14 projects downwardly covering, protecting and shielding the eyes.

To distribute any forces resulting from an object impacting the lens 14, the lowermost extent of the lens 14 as shown in FIGS. 1 and 4 angles outwardly from the face to define a border 26. The lens 14 is contoured such that the border 26 is spaced from, but follows the contour of, the face over the cheeks and nose bridge 28 and 30 respectively. By virtue of the lens 14 being contoured such that the upper margin 18 is supported against the forehead, whereas the remainder of the lens including the border 26 is spaced from the face, air is permitted to circulate beneath the lens 14 to prevent fogging of the lens 14. In the event that an object strikes the lens, the lens 14 will be displaced toward the face such that the border 26 bears against the face along a strip running over the cheeks 28 and nose bridge 30 to distribute the impact of the object over such strip and along the upper margin 18. As can be appreciated, by virtue of the location and spanse of the border 26, such a distribution of the force between the border 26 and face and upper margin 18 and forehead reduces the risk of injury to the nose.

Figure 5:
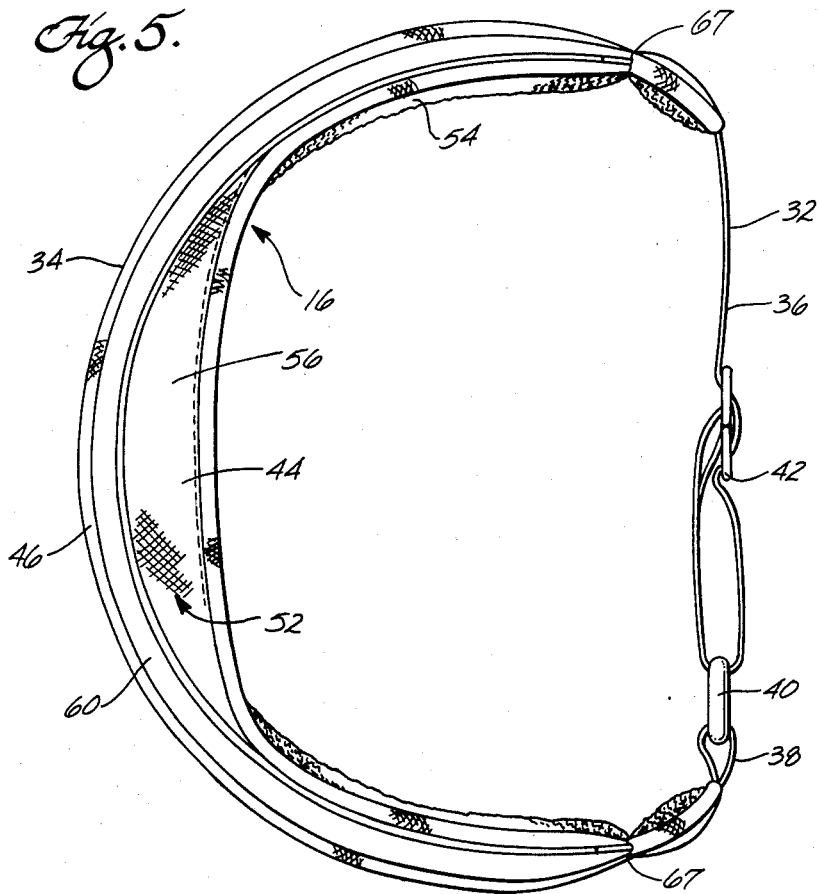
FIG. 5 is a bottom view of the headband adapted to mount the lens of FIG. 4.

To attach the headband 16 and lens 14 to the head, the headband 16 includes an adjustable elastic strap 32 connected to a brow band 34. The elastic strap 32 as shown in FIG. 5 consists of an adjustable member 36 and a fixed loop 38. As is known in the art, an eyelet 40 interconnects the adjustable member 36 to the loop 38, the adjustable member 36 including a buckle 42 enabling the strap 32 to be lengthened or shortened to expand or contract the girth of the headband 16. Of course it is to be understood that other types of adjustable straps such as those having snaps or strip-type connectors may be used. The adjustable member 36 is preferably elastic to impart such elastic properties to the headband 16 for contraction about the head 12 to hold the eyeshield 10 thereto. Alternatively, an adjustable non-elastic strap could be substituted for the elastic strap 32.

To removably mount a selected lens 14 to the headband 16 and for other purposes which will hereinafter become evident, the brow band 34 is provided. The brow band 34 is somewhat elastic and extends approximately from temple to temple about the forehead. Viewing FIGS. 3 and 5 it can be seen that the brow band 34 includes an inner panel 44 connected to an outer panel 46 by suitable connection means such as stitching. The panels are connected so as to define a downwardly opening pocket 52 to receive the lens upper margin 18 as described in detail below.

The inner panel 44 has an absorbent strip 54 adapted to absorb perspiration and provide a comfortable surface to rest against the forehead. The absorbent strip 54, in addition to being absorbent and comfortable, defines a sufficiently high friction coefficient between itself and the forehead to prevent the brow band 34 from sliding along the forehead. It has been found that terrycloth is particularly well suited for the absorbent strip 54 in that it is absorbent, comfortable against the skin and is washable. In addition to the absorbent strip 54, the inner panel 44 includes a backing strip 56, again, preferably fashioned from a cloth material. The backing strip 56 defines the rearmost boundary of the pocket 52, and may be fashioned from cotton, cotton blend or synthetic fibers.

To cushion the lens 14 against the forehead, maintain the shape of the inner panel 44, and to provide a degree of elasticity to the brow band 34, the inner panel 44 is provided with cushion means embodied as a cushion strip 58 trapped between the absorbent strip 54 and the backing strip 56. The cushion strip 58 is preferably foam rubber to enhance the machine washability of the headband. Viewing FIG. 3 it can be seen that the cushion strip 58 also imparts comfort and shock absorbing qualities to the inner panel 44.

To interconnect the absorbent strip 54 and backing strip 56 to trap the cushion strip 58 therebetween, connection means such as stitching 60 along the upper and lower edges of such strips is provided. To enhance the strength of the band between the absorbent and backing strips and prevent fraying, a hem strip 62 is cooperatively stitched with and over the lower edges of absorbent and backing strips 54 and 56, the hem strip defining an inner lip of the pocket 52.

The outer panel 46 is similar in construction to the inner panel 44 including a strip preferably of cloth material defining a front piece 61 for the brow band 34. The front piece 61 may be of any suitable and fashionable fabric and color or may be provided with promotional lettering or the like. Behind the front piece 61 the outer panel also includes a strip preferably of cloth material defining a liner 62. The liner 62 defines the other boundary of the pocket 52 and may consist of terrycloth material. The liner 62 with the backing strip 56 of the inner panel 44 bear against the lens upper margin 18 shown in FIG. 3 and as described below.

To maintain the shape of the outer panel 46 and to provide a degree of elasticity to the brow band, an intermediate layer 63 of a suitable material such as foam rubber is disposed between the front piece 61 and the liner 62. As shown on the drawings, the intermediate layer 63 may include a greater amount of material to provide a greater degree of support for the overall shape of the brow band 34. To interconnect the front piece 61 and the liner 62 a pair of hem strips 64, which may be of different colors to enhance the fashionable appearance of the headband 16, are stitched over and with the upper edges of the front piece 61 and liner 62 with suitable stitches 63. The stitching of the uppermost hem strip 64 simultaneously interconnects the inner and outer panels 44 and 46 along their upper extent. The lowermost hem strip 64, which defines an outer lip for the pocket 52, enhances the strength and prevents fraying of the outer panel 46 which would otherwise occur during wearing or laundering.

Figure 6:
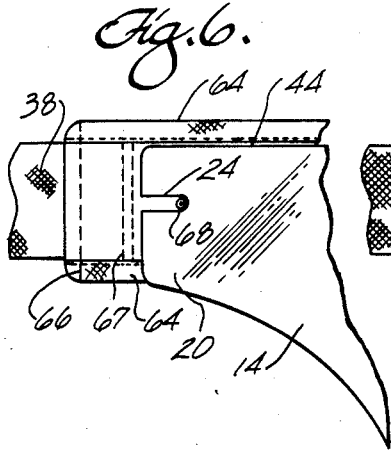
FIG. 6 is a section view of a portion of the eyeshield showing the interconnection of the lens to the headband.

To further connect the inner and outer panels their mutual ends adapted to overlay the temples may be connected by two spaced lines 66 and 67 of stitching as shown in FIGS. 5 and 6. These lines 66 and 67 of stitching also attach the adjustable strap member 36 and loop 38 to the brow band 34. As can be appreciated, the foregoing construction of the brow band 34 defines the pocket 52 between stitching 67 bordered by the inner and outer panels 44 and 46, such panels being somewhat elastic.

For purposes which will hereinafter become evident, a tack 68 of thread is sewn between the outer and inner panels 44 and 46 through the pocket 52 near its ends adjacent the lines of stitching 66 and 67. Alternatively, a pin or a rivet could be used in place of the tack 68.

As can be appreciated, the headband 16 as described above is relatively inexpensive to manufacture, is comfortable, washable, and can be provided with any desired fashionable appearance. As can further be appreciated, the fabric which defines the inner and outer panels 44 and 46 is somewhat elastic and can be stretched to increase the overall arcuate length of the pocket 52 and thereby the distance between the tacks 68. This feature, as set forth below, is important for the interchangeable connection of lenses to the headband.

To connect a selected lens 14 to the headband 16 one of the margin ends, for example the right end 20 as shown in FIG. 6, is positioned in the pocket 52 until the tack 68 is received into its dedicated slot 24. Thereafter, the brow band 34 is somewhat stretched so as to position the entire upper margin 18 of the lens 14 within the pocket 52 and such that the left end 22 is disposed for registry of the tack 68 with its slot 24. After so positioning the upper margin 18 within the pocket 52 the brow band 34 is released, whereupon it contracts, causing the dedicated tack 68 to be received into the slot 24 at the left end 22, securely mounting the lens 14 to the headband 16. To enhance the interconnection between the lens 14 and headband 16, an adhesive strip 70 which may be embodied as double stick tape, i.e., a suitable tape strip carrying pressure-sensitive adhesive on both sides, can be provided along the upper margin of the lens 18 to bond the liner 62 of the outer panel 46 to the lens 14.

As can be seen, the eyeshield 10 according to the above construction is highly versatile in that any one of a population of lenses designed for a particular use or uses (FIG. 8) may be interconnected to any one or a population of headbands. For example, a series of lenses provided with progressively darker tints may be provided to enable the user to interconect the lens to provide the desired degree of eye shading. Also, a population of lenses and headbands of different colors and tints may be provided so that the eyeshield may be color coordinated with the individual's clothing. Still another advantage is that the eyeshield is relatively inexpensive to manufacture, since the interchangeability does not require exacting manufacturing tolerances. Still another advantage is that the headband may easily be removed from the lens for laundering thereof or, if desired, for use apart from a lens. Over and above the foregoing advantages, the contour of the lens, and more particuarly its border, is adapted to distribute forces resulting from objects impacting the lens over a large area to prevent injury to the face.

Figure 7:
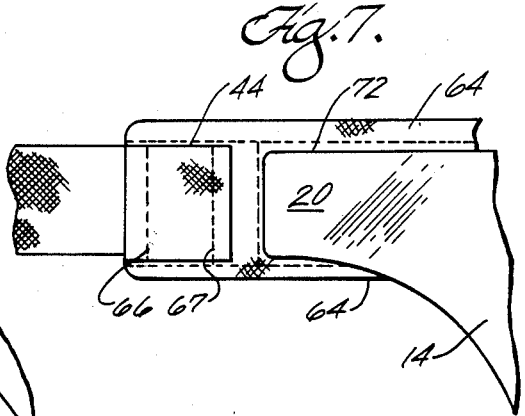
FIG. 7 is a view similar to that of FIG. 6 showing a further embodiment of the interconnection between the lens and the headband.

Turning to FIG. 7 an alternative embodiment is shown. In lieu of providing a slot at one of the ends of the upper margin, one of the tabs 20 or 22 may be designed to be received into the pocket 52 and more particularly a recess 72 defined at one end thereof by suitable stitching. Accordingly, to interconnect such a lens 14 to the headband 16, the tab 20 of FIG. 7 is first inserted into its respective recess 72. The brow band 34 is then stretched to position the entire upper margin 18 within the pocket 52 and released such that the tack 68 at the other end 22 of the brow band 34 is received into the respective slot 24 of the other end 22 of the upper margin 18.

While I have shown and described certain embodiments of the present invention it is to be understood that it is subject to many modifications without departing from the scope and spirit of the claims, as hereinafter set forth.

What is claimed is:

1. An eyeshield comprising:
a transparent lens adapted to cover and protect the eyes, the lens having an uppermost margin to extend about the frontal portion of the head to terminate at opposite ends, at least one of such ends including a slot; and a headband at least a portion of which includes semi-elastic inner and outer panels connected to define a pocket adapted to expand lengthwise and removably receive the margin for interconnection of the headband and lens, a tack provided between the panels through the pocket and disposed to be located proximate the slot when the pocket is expanded, release of the pocket causing said pocket to elastically contract to position said tack in the slot to secure the lens in the pocket.

2. The eyeshield of claim 1 wherein each of such margin ends includes a slot, the headband including a pair of tacks disposed between the panels, each tack adapted to be positioned proximate a slot when the pocket is expanded and received by a slot when the pocket contracts to mount the lens.

3. The eyesheild of claim 1 further including adhesive disposed along the upper margin to adhere one of such panels to the upper margin.

4. The eyeshield of claim 1 wherein the inner panel includes an absorbent strip of material adapted to overlay the frontal portion of the head and absorb perspiration.

5. The eyeshield of claim 4 wherein the inner panel further includes a fabric backing strip connected to the absorbent strip and a cushion strip interposed between such absorbent strip and backing strip, the cushion strip adapted to cushion the lens upper margin against the forehead.

6. The eyeshield of claim 1 wherein the lens includes a lower border adapted to, upon displacement of the lens when impacted by an object, engage the face over a strip which extends over the cheeks and nose bridge to distribute the force of such impact.

7. An eyeshield comprising:
   a population of transparent lenses each adapted to cover and protect the eyes and each lens having an uppermost margin to extend about the forehead and terminate at opposite ends, each such end including a slot; and
   at least one headband, a portion of which defines a semi-elastic brow band including inner and outer panels connected to define a pocket adapted to expand lengthwise to removably receive the margin of each lens, and tacks provided in the pocket each positioned for location in a slot when the pocket is expanded, contraction of the pocket causing a tack received into each slot to removably secure a selected lens to the brow band.

8. The eyeshield of claim 7 further including an adhesive strip along each lens upper margin to adhere the brow band to each lens.

9. The eyeshield of claim 7 wherein the headband is fashioned from launderable fabric.

10. The eyeshield of claim 7 wherein each lens has a border remote from its uppermost margin, the border fashioned to bear substantially equally over a strip extending over the cheeks and nose bridge when the lens is impacted, to distribute the force of such impact.

11. The eyeshield of claim 7 wherein the inner panel includes an absorbent strip to bear against the forehead to absorb perspiration.

12. The eyeshield of claim 11 wherein the absorbent strip is terrycloth.

13. An eyeshield comprising:
   a transparent lens adapted to cover and protect the eyes, the lens having an uppermost margin to extend about the frontal portion of the head to terminate at each end at a projecting tab, at least one said tabs including a slot; and
   a headband at least a portion of which includes semi-elastic inner and outer panels connected to define a downwardly open pocket expandable to receive said uppermost margin and tabs and elastically contractable to retain said uppermost margins and tabs to removably secure said lens to said headband, the headband including a tack positioned through the pocket, said track located and said slot configured such that said tack is positioned to be received by said slot when the pocket is expanded, elastic contraction of the pocket locating the tack in the slot.

* * * * *